US008323904B2

(12) United States Patent
Miyake et al.

(10) Patent No.: US 8,323,904 B2
(45) Date of Patent: Dec. 4, 2012

(54) KIT FOR MEASUREMENT OF TERMITE INSECTICIDE ACTIVE INGREDIENT BY IMMUNOASSAY METHOD

(75) Inventors: Shiro Miyake, Kyoto (JP); Mikiko Uchigashima, Kyoto (JP); Atsushi Kadowaki, Kyoto (JP)

(73) Assignee: Bayer Cropscience AG, Monheim am Rhein (DE)

( * ) Notice: Subject to any disclaimer, the term of this patent is extended or adjusted under 35 U.S.C. 154(b) by 636 days.

(21) Appl. No.: 12/097,627

(22) PCT Filed: Dec. 14, 2006

(86) PCT No.: PCT/JP2006/324930
§ 371 (c)(1),
(2), (4) Date: Nov. 4, 2009

(87) PCT Pub. No.: WO2007/069681
PCT Pub. Date: Jun. 21, 2007

(65) Prior Publication Data
US 2010/0047927 A1    Feb. 25, 2010

(30) Foreign Application Priority Data

Dec. 16, 2005  (JP) ................................ 2005-363166
Nov. 15, 2006  (JP) ................................ 2006-309332
Dec. 8, 2006   (JP) ................................ 2006-332073

(51) Int. Cl.
*G01N 33/53* (2006.01)
(52) U.S. Cl. ........................................ 435/7.1; 436/518
(58) Field of Classification Search .................. None
See application file for complete search history.

(56) References Cited

U.S. PATENT DOCUMENTS

| | | | |
|---|---|---|---|
| 4,770,853 A | 9/1988 | Bernstein | 422/58 |
| 5,169,789 A | 12/1992 | Bernstein | 436/501 |
| 5,215,102 A | 6/1993 | Guirguis | 128/771 |
| 5,356,785 A | 10/1994 | McMahon et al. | 435/7.92 |
| 6,495,352 B1 * | 12/2002 | Brinker et al. | 435/176 |
| 2003/0064389 A1 | 4/2003 | Goda et al. | |
| 2003/0108970 A1 | 6/2003 | Brady et al. | |

FOREIGN PATENT DOCUMENTS

| | | |
|---|---|---|
| CA | 2 385 735 A1 | 11/2002 |
| EP | 0 645 628 | 3/1995 |
| EP | 1 235 805 B1 | 9/2002 |
| EP | 1 258 729 A2 | 11/2002 |
| GB | 1 506 017 | 4/1978 |
| JP | 55-121135 | 9/1980 |
| JP | 1-502054 | 7/1989 |
| JP | 1-245157 | 9/1989 |
| JP | 6-504130 | 5/1994 |
| JP | 07181181 | 7/1995 |
| JP | 9072898 | 3/1997 |
| JP | 2000191698 | 7/2000 |
| JP | 2003516423 | 6/2002 |
| JP | 200338173 | 12/2003 |
| WO | WO-01/42787 A2 | 6/2001 |

OTHER PUBLICATIONS

Pulido-Tofino et al. (Analytical Chimica Acta 2001 vol. 429, p. 337-345).*
Nichkova et al. (Anal. Chem. 2005 vol. 77, p. 6864-6872-3).*
Office Action issued in Australian Patent Application No. 2006325990, mailed Mar. 31, 2011.
Supplemental International Preliminary Report on Patentability issued during the prosecution of International Application No. PCT/JP2006/324930, 2006.
Hennion et al., "Immuno-Based Sample Preparation for Trace Analysis," J Chromatogr A. Jun. 6, 2003;1000(1-2):29-52.
Morozova et al., "Determination of Pesticides by Enzyme Immunoassay," Journal of Analytical Chemistry, Mar. 2005. vol. 60(3) p. 202-217.
Proenca et al., "Two Fatal Intoxication Cases With Imidacloprid: LC/MS Analysis," Forensic Sci Int. Oct. 4, 2005;153(1):75-80.
Shan et al., "Development of an Immunoassay for the Pyrethroid Insecticide Esfenvalerate," J Agric Food Chem. May 1999;47(5):2145-55.
Supplementary European Search Report issued Apr. 21, 2009, during the prosecution of Application No. EP 06 83 4684.
Watanabe et al, "Evaluation of a Commercial Immunoassay for the Detection of Chlorfenapyr in Agricultural Samples by Comparison With Gas Chromatography and Mass Spectrometric Detection," J Chromatogr A. May 13, 2005;1074(1-2):145-53.
Watanabe et al., "Rapid and Simple Screening Analysis for Residual Imidacloprid in Agricultural Products With Commercially Available ELISA," Analytica Chimica Acta. vol. 521, Issue 1, Sep. 6, 2004, pp. 45-51.
Office Action issued in Japanese Patent Application No. 2006-309332, issued Aug. 5, 2011.
Yu et al., "Determination of fipronil in water by ELISA based on monoclonal antibody," *Acta Scientiae Circumstantiae*, English Abstract, 24(5):910-914, 2004.
Office Action issued in Australian Patent Application No. 2006325990, mailed Dec. 23, 2011.
Office Action issued in Japanese Application No. 2006-309332, issued Aug. 5, 2011, and English language translation thereof.
Office Action issued in Japanese Application No. 2006-309332, issued Feb. 24, 2012, and English language translation thereof.
Decision of Refusal, issued Jun. 7, 2012 (published Jun. 7, 2012) during the prosecution of Japanese Patent Application No. 2006-309332.

* cited by examiner

Primary Examiner — Jacob Cheu
(74) Attorney, Agent, or Firm — Fulbright & Jaworski L.L.P.

(57) ABSTRACT

A kit and a method are provided for easily measuring the concentration of an active ingredient of a termite insecticide persisting in soil, particularly on site where a termite insecticide was actually applied. A kit of the present invention comprises 1) an extraction unit for extracting, with an solvent, a termite insecticide active ingredient from an object of measurement and 2) a reaction unit including a reaction container for encapsulating an identifying antigen, a fixing member for immobilizing an antibody against an active ingredient, and a sealing member capable of fitting to the reaction container. The kit optionally includes 3) a detection unit for visually or optically detecting a change depending on the concentrations of the active ingredient in the object of measurement, and 4) a dilution unit for diluting the sample solution to a certain ratio.

12 Claims, 3 Drawing Sheets

(A)

(B)

(C)

(D)

KIT FOR MEASUREMENT OF TERMITE INSECTICIDE ACTIVE INGREDIENT BY IMMUNOASSAY METHOD

This Application is a National Phase Application of International Application No. PCT/JP2006/324930 filed Dec. 14, 2006, which claims priority to Japanese Patent Application Serial No. 2005-363166, filed Dec. 16, 2005; Japanese Patent Application Serial No. 2006-309332, filed Nov. 15, 2006; and Japanese Patent Application Serial No. 2006-332073, filed Dec. 8, 2006, all of which applications are incorporated by reference herein in their entirety.

FIELD OF INVENTION

The present invention relates to a kit for measurement of a termite insecticide by using an immunoassay method. The present invention is useful as a kit for easily measuring the concentration of a termite insecticide persisting in soil such as fipronil or imidacloprid, particularly on site where a termite insecticide was actually applied.

BACKGROUND ART

A termite insecticide is applied or sprayed onto a base or under floor in constructing an object building and should thereafter have residual effectiveness for a long time in soil etc., and thus requires periodical monitoring of concentration. With respect to the form of an active ingredient of a termite insecticide, there are cases where the active ingredient is contained in an emulsion or capsule preparations such as microcapsules.

Conventionally, the concentration of a residual active ingredient in a termite insecticide has been analyzed by extracting a termite insecticide component from e.g. soil as the object, purifying the component and measuring it by gas chromatography (GC). That is, usually the sample is extracted with an organic solvent, purified through a plurality of columns such as porous diatomaceous earth column, florisil column, silica gel column, $C_{18}$ column, and florisil column in order and then measured by GC. Such measurement method is satisfactory in respect of accuracy and sensitivity, but requires expensive facilities and sophisticated techniques and is thus not suitable for outside measurement.

Immunoassay methods, on the other hand, comprise measuring an antigen by utilizing the specific reactivity of an antibody against the antigen, and is thus excellent in measurement accuracy without requiring a complicated purification step or expensive facilities such as in the above-mentioned GC, thus making the measurement methods rapid, easy and economical. Conventionally, immunoassay methods play an important role in analyzing clinical states of patients in the field of clinical diagnosis, and in recent years, application thereof to measurement of environmentally burdening chemical substances is advancing. For some termite insecticides, a method of immunologically measuring an active ingredient of a termite insecticide, which comprises using a monoclonal antibody produced with the use of, as immunogen, a conjugate of a derivative of the active ingredient to which a protein was bound thereto, has been developed (for example, Japanese Patent Application Laid-Open No. 2000-191698).

The substance used as an active ingredient of a termite insecticide includes organophosphorus-based insecticides such as chlorpolis, fenitrothion and pyridaphenthion, pyrethroid-based permethrin and tralomethrin, creosote oil that is a mixture of cresol and naphthalene, phenylpyrazol-based fipronil, and neonicotinoid-based imidacloprid.

Patent Document 1: Japanese Patent Application Laid-Open No. 2000-191698

SUMMARY OF THE INVENTION

Problems to be Solved

The conventional GC analysis methods used in measurement of an active ingredient of a termite insecticide requires complicated procedures and time for the process for extraction and purification of a sample. Further, analysis equipment furnished with a measurement apparatus and equipment to which high costs have been invested are required in measurement. Accordingly, GC cannot be applied for confirmation of residual effectiveness on site where a termite insecticide was applied.

The immunoassay method, on the other hand, does not require a complicated purification process, and is thus a measurement method comparatively suitable for on-site measurement. However, the immunoassay method utilizing a typically used microplate is suitable in analysis facilities as well, and cannot be used in a method that suits for a housing area where a termite insecticide was applied.

Further, when the active ingredient is present as a capsule preparation such as microcapsule, the ingredient cannot be measured without dissolving a capsule portion, so there is demand for an easier measurement method on an application site.

The objective of the present invention is to provide a method and kit for measuring a termite insecticide by an immunoassay method, which is excellent in operativeness in measurement in a site where a termite insecticide was applied.

Means to Solve the Problems

As a result of extensive study, the present inventors found that the objective can be achieved by a kit for measurement of a termite insecticide by an immunoassay method as shown below, and the present invention was thereby arrived at.

That is, the present invention provides a kit for measurement of an active ingredient of a termite insecticide by an immunoassay method, which comprises:
1) an extraction unit for extracting, with an solvent, a termite insecticide active ingredient from an object of measurement, and 2) a reaction unit including a reaction container for encapsulating an identifying antigen, a fixing member for immobilizing an antibody against an active ingredient, and a sealing member capable of fitting to the reaction container.

In the kit for measurement of an active ingredient of a termite insecticide by the immunoassay method according to the present invention, the identifying antigen is a conjugate consisting of a hapten of a termite insecticide active ingredient and a substance having an identifying function, and the antibody can be a monoclonal antibody or a fragment thereof.

The kit for measurement of an active ingredient of a termite insecticide by the immunoassay method according to the present invention can employ, as the reaction container, a combination of at least one reaction container in which an identifying antigen is encapsulated and at least one reaction container in which an identifying antigen and a termite insecticide active ingredient of known amount are encapsulated.

In the kit for measurement of an active ingredient of a termite insecticide by the immunoassay method according to the present invention, the identifying antigen and a mixture of the identifying antigen and a termite insecticide active ingredient of known amount can be previously encapsulated in a dried state in the reaction containers, respectively, and in the reaction container in which the identifying antigen only is encapsulated, the identifying antigen can be dissolved in the sample solution, and in the reaction container in which the mixture is encapsulated, the mixture can be dissolved in a dissolving liquid.

In the kit for measuring an active ingredient of a termite insecticide by using the immunoassay method of the present invention, the reaction unit can also have a detection function for visually or optically detecting a change depending on the concentration of a termite insecticide active ingredient in a sample.

Alternatively, the kit for measuring an active ingredient of a termite insecticide by using the immunoassay method of the present invention can further include a detection unit for visually or optically detecting a change depending on the concentration of a termite insecticide active ingredient in a sample.

The kit for measuring an active ingredient of a termite insecticide by using the immunoassay method of the present invention can optionally include a dilution unit for diluting to a predetermined ratio a sample solution extracted in the extraction unit.

The kit for measurement of an active ingredient of a termite insecticide by using the immunoassay method of the present invention can include a solvent in the extraction unit. This solvent can be a member selected from the group consisting of ethanol, methanol and dimethyl sulfoxide, or a mixture of two or more thereof.

In the present invention, the object of measurement can be a material contained in a capsule preparation. The capsule preparation can be in the form of a microcapsule.

The method of measuring an active ingredient of a termite insecticide by the immunoassay method of the present invention comprises the steps of: 1) extracting, with a solvent, a termite insecticide active ingredient from a measurement object collected, 2) contacting the termite insecticide active ingredient-containing sample solution obtained in the above extraction step, with a fixing member having an antibody against an active ingredient immobilized thereon in a reaction container in which an identifying antigen was encapsulated, and 3) detecting, by the antigen-antibody reaction upon the above contact, a change depending on the concentration of the termite insecticide active ingredient in the sample.

In the method of measuring a termite insecticide active ingredient by the immunoassay method of the present invention, the identifying antigen is a conjugate of a hapten of a termite insecticide active ingredient conjugated with a substance having an identifying function, and the antibody can be a monoclonal antibody or a fragment thereof.

The detection step can be a step of comparing a change in the sample solution obtained in the extraction step, with a change in a sample solution containing a predetermined amount of a termite insecticide active ingredient.

In the present invention, the termite insecticide active ingredient can be fipronil or imidacloprid.

Fipronil (chemical name: 5-amino-1-(2,6-dichloro-4-(trifluoromethyl)phenyl)-4-((trifluoromethyl) sulfinyl)-1H-pyrazol-3-carbonitrile has a structure represented by the following formula (1):

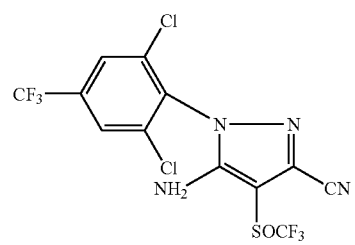

[Formula 1]

and is used not only as a termite insecticide but also as an insecticide to exhibit an excellent pharmaceutical effect on a wide spectrum of agricultural harmful insects such as Hemiptera harmful insects such as Auchenorrhyncha, Sternorrhyncha, Pseudococcidae, Pentatomidae, Pseudococcidae and *Ceroplastes ceriterus*, Lepidoptera harmful insects such as Bostryehdae, *Caloptilia zachrysa*, *Phyllonorycter ringoniella* Matsumura, *Lyonetia prurifoliella*, *Lyonetia clerkella* L., and *Phyllocnistis citrella*, and coleoptera harmful insects and orthoptera harmful insects and has permeation migration and residual effectiveness.

Imidacloprid (chemical name: 1-(6-chloro-3-pyridylmethyl)-N-nitroimidazolidin-2-ylideneamine)) has a structure represented by the following formula (2):

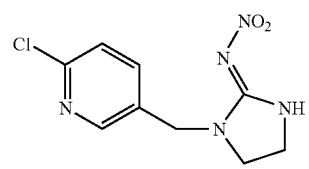

[Formula 2]

and has a fast-acting insecticidal activity. More specifically, imidacloprid is estimated to act on a nicotinic acetylcholine receptor on a postsynaptic membrane, thus blocking neurotransmission. Harmful insects exposed to this chemical are killed through paralysis and relaxation symptoms unlike abnormal excitation caused by conventional organophosphorus chemicals or carbamates. Even at or below lethal concentration, imidacloprid can suppresses activities such as eating, mating behavior, egg production, flying and walking of harmful insects (Agrichemical Handbook, pp. 116-118 and p. 538, 1994, Japan Plant Protection Association; Latest Agrichemical Residue Analysis Method, pp. 355-357, edited by Study Group of Agrichemical Residue Analysis and published by Chuo Hoki Shuppan). This compound is used not only as a termite insecticide but also as an insecticide to exhibit an excellent pharmaceutical effect on a wide spectrum of agricultural harmful insects such as Hemiptera harmful insects such as Auchenorrhyncha, Sternorrhyncha, Pseudococcidae, Pentatomidae, Pseudococcidae and *Ceroplastes ceriterus*, Lepidoptera harmful insects such as Bostryehdae, *Caloptilia zachrysa*, *Phyllonorycter ringoniella* Matsumura, *Lyonetia prurifoliella*, *Lyonetia clerkella* L., and *Phyllocnistis citrella*, and coleoptera harmful insects and orthoptera harmful insects and has permeation migration and residual effectiveness.

Effects of the Invention

By applying the present invention, there can be provided a kit or method for measuring a termite insecticide active ingredient by an immunoassay method which is highly selective for an active gradient of a termite insecticide in various forms applied to soil and is excellent in operativeness even on an application site.

EXPLANATION OF THE SYMBOLS

Figure 1:
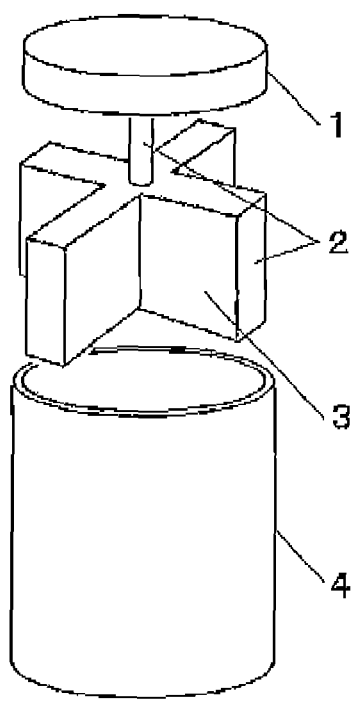
FIG. 1 shows specific example of a reaction container of the present invention.
Figure 1:
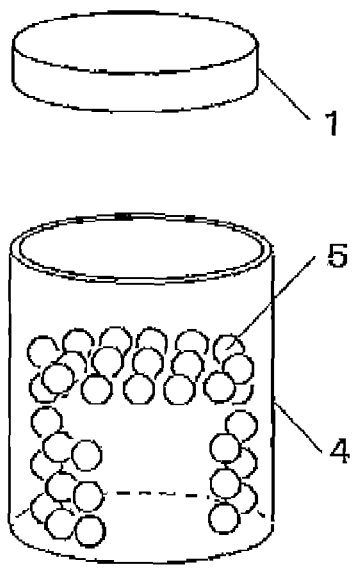
Figure 1:
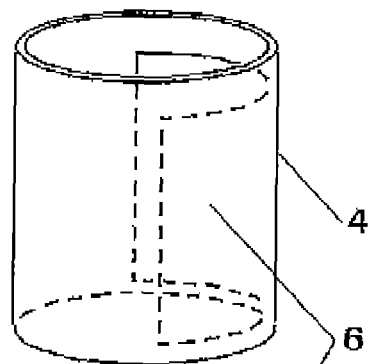
Figure 1:
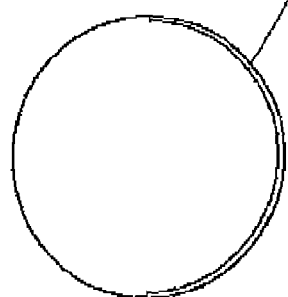
Figure 1:
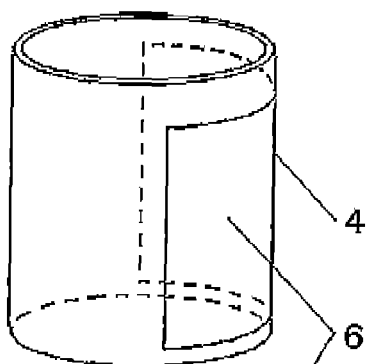
Figure 1:
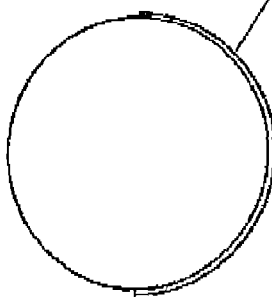

1. Sealing member (lid-shaped part)
2. Fixing member (stick shaped part)
3. Top part
4. Reaction container
5. Fixing member (carrier)
6. White member

DETAILED DESCRIPTION OF THE INVENTION

Hereinafter, embodiments of the present invention are described.

The immunoassay method utilizing the antigen-antibody reaction is an easily operated measurement method capable of high-sensitivity measurement generally with high selectivity for a specific substance. In the present invention, such feature is utilized while the shape of a kit, a means of immobilizing an antibody involved in the reaction, a means of contacting and operating reactants, and a means of detecting a reaction state in measurement of a termite insecticide active ingredient are selected, thereby enabling the constitution of a measurement kit in which the optimum operation is feasible even on site.

That is, a reaction container in which an identifying antigen contributing to the reaction is encapsulated under stable conditions is prepared, and in the reaction container, all procedures are made feasible, whereby an easy measurement kit excellent in operativeness and stability can be constituted. Specifically, in the first step, a termite insecticide active ingredient is extracted from a measurement object, and then the prepared sample is introduced into the reaction container having an identifying antigen encapsulated therein, whereby the termite insecticide active ingredient in the sample can be uniformly mixed with the identifying antigen. Then, in the second step, a carrier with an antibody against the termite insecticide active ingredient immobilized thereon is inserted or introduced into the reaction container, whereby competitive antigen-antibody reaction between the termite insecticide active ingredient and the identifying antigen can be rapidly and reliably effected. In the third step, for example, a reaction product obtained by such reaction is detected as coloration reaction derived from the identifying antigen bound to the antibody, thereby optically detecting a change depending on the concentration of the termite insecticide active ingredient in the sample, whereby the concentration of the termite insecticide active ingredient can be determined. The competitive reaction and coloration reaction can be carried in the sealed container in order to facilitate outdoor operation. As described above, the present invention is characterized in that all procedures such as stirring, reaction and measurement are carried out in the reaction container having the identifying antigen previously sealed therein.

As used herein, the phrase "visually or optically detecting" refers to detection wherein a change accompanying the antigen-antibody reaction, that is, coloration or fluorescence generated by the reaction itself or coloration or fluorescence generated by adding a coloring agent or a fluorescent agent, or turbidity, is detected as an optical change with the eye observation or with an absorptiometer.

That is, these means are combined while the feature of the immunoassay method is utilized, and the shape of a reaction container, a method of forming a pharmaceutical preparation of a reagent involved in the reaction, a means of contacting and operating reactants, and a means of detecting a reaction state are selected, thereby enabling the constitution of a measurement kit which can be preferably used even on a site where the termite insecticide active ingredient is applied.

For generation of competitive reaction of the identifying antigen with a termite insecticide active ingredient as the measurement object in the immunoassay method, a substance having a molecular structure similar to that of the termite insecticide active ingredient and having an epitope that can induce an antibody production is preferably used as the identifying antigen. In the present invention, the identifying antigen is a conjugate of a derivative of the termite insecticide active ingredient conjugated with a substance having an identifying function, thereby satisfying this condition and enabling highly selective measurement. As used herein, the "substance having an identifying function" refers to a substance or carrier capable of directly or indirectly identifying the result of antigen-antibody reaction, and specific examples include biological substances such as enzyme and fluorescent protein, low-molecular fluorescent substance, and carriers such as gold colloid and color latex bead. In the antigen-antibody reaction in the present invention, not only an intact antibody but also an antigen-binding part of a fragment such as Fab fragment and F(ab')2 fragment is contained.

The active ingredient of a termite insecticide may be any of compounds such as chlorpolis, fenitrothion, pyridaphenthion, permethrin, tralomethrin, creosote oil that is a mixture of cresol and naphthalene, fipronil, imidacloprid, thiamethoxiam, clothianidin, and dinotefuran. For detection of these compounds, each compound is used as it is, or a derivative thereof which is bound to a labeling substance is used in the immunoassay method of the present invention.

In the measurement kit or method of the present invention, the result of antigen-antibody reaction is detected as a visual or optical change such as coloration. Therefore, the standard for the concentration of a termite insecticide active ingredient in a sample is preferably clarified. Accordingly, a plurality of reaction containers in which a termite insecticide active ingredient of various known concentrations including zero are encapsulated can be prepared and compared for coloration with the reaction container into which the sample solution was introduced, whereby measurement free of the influence of background or ambient temperature is feasible. That is, by comparison with the standard having common measurement conditions, a measurement kit or method for a termite insecticide active ingredient by using an easy and highly accurate immunoassay method can be provided.

Generally speaking, among agents used as the identifying antigen, some agents are lacking in long-term stability when left unattended. When such deterioration occurs, not only the reaction rate but also the reaction itself is influenced as the degree of activity is lowered, and thus measurement accuracy can be significantly influenced in some cases. It was found in the present invention that the identifying antigen is lyophilized, whereby the agent is prevented from being deteriorated, and the optimum reaction can be secured just before use, and in the reaction container, the identifying antigen is dissolved with a sample solution or a diluted sample solution (referred to hereinafter as "sample solution") or a dissolving liquid, and simultaneously the antigen-antibody reaction is initiated to enable measurement of a termite insecticide active ingredient by using the rapid immunoassay method. The reaction can be initiated and completed in the reaction container, and thus a measurement kit excellent in on-site operativeness can be constituted. The "dissolving liquid" is a solvent which like a diluent, is not involved in the reaction and is used in dissolving the previously lyophilized identifying antigen or a mixture of the identifying antigen and a termite insecticide active ingredient of known amount.

In the present invention, the visual or optical change such as coloration as a result of the antigen-antibody reaction can also be detected in the reaction unit or by arranging another detection unit. The present invention may include a dilution unit for diluting, to a predetermined ratio, the termite insecticide active ingredient-containing sample solution prepared in the extraction unit, and by this dilution unit, the sample solution extracted from the measurement object can be diluted suitably to a concentration suitable for the reaction.

In the present invention, the solvent contained in the extraction unit can be a member selected from the group consisting of methanol, ethanol and dimethyl sulfoxide or a combination of two or more thereof. In one mode, the object of measurement contains a capsule preparation, and this capsule preparation can be in the form of a microcapsule.

The present invention includes the case in which a termite insecticide such as a termite insecticide active ingredient is encapsulated in a microcapsule. The influence of a termite insecticide on the human body can be minimized by capsulation, while for the termite, the microcapsule is incorporated in its mouth by grooming and then crushed into the body of the termite, whereby an active ingredient in the microcapsule exert its' effect. Accordingly, capsulation techniques including microcapsules have been used in recent years. Therefore, it is necessary to accurately measure the amount of the termite insecticide active ingredient in the capsule preparation, and it is important to select a solvent both for dissolving the capsule portion in the sample and for extracting the termite insecticide active ingredient.

<Fundamental Constitution of the Measurement Kit of the Present Invention and Measurement Method>

The kit for measurement of a termite active ingredient by using the immunoassay method of the present invention comprises (1) an extraction unit for preparing a termite insecticide active ingredient-containing sample solution extracted with a solvent from a measurement object collected, (2) a reaction unit including a reaction container for encapsulating an identifying antigen, a fixing member for immobilizing an antibody against the termite insecticide active ingredient, and a sealing member capable of fitting to the reaction container, wherein the antigen-antibody reaction is carried out by contacting with the sample solution.

By combining these means, the feature of the immunoassay method is utilized while the shape of the reaction container, the method of forming a pharmaceutical preparation of the reagent involved in the reaction, the method of contacting the reactants, and the method of detecting the reaction state are selected thereby enabling the constitution of a measurement kit which can be preferably used in a site where the termite insecticide active ingredient was applied.

In the measurement method of using the measurement kit of the present invention, usual immunoassay methods, for example, a known enzyme immunoassay method, a gold colloid method etc. (Meth. Enzymol., 92, 147-523 (1983), Antibodies, Vol. II IRL Press Oxford (1989)) can be used.

Hereinafter, each unit as a fundamental constitution of the measurement kit of the present invention is described by reference to one embodiment in which application of antibody solid phase type ELISA (enzyme-linked immunosorbent assay) among the enzyme immune measurement methods is applied, but the present invention is not limited thereto. The respective materials etc. described herein are not limited to those of the measurement kit to which ELISA is applied, and are common among measurement kits in the case where other label is used as well as are common among other measurement methods of using ELISA or other label. The measurement object can include soil and environmental water, and the measurement substance is a termite insecticide active ingredient.

(1) Extraction Unit

For example, soil is added to a solvent in a container made of glass or resin such as polypropylene or polyethylene and then stirred, whereby a termite insecticide active ingredient is extracted. The solvent for extraction includes methanol, acetone, acetonitrile, ethyl acetate, ethanol, dimethyl sulfoxide, and dimethylformamide. Such solvent may be previously introduced into the container or contained separately in the kit. Alternatively, the kit includes a container only, and the solvent may be separately obtained. The preferable concentration of the solvent is about 30 to 100%. That is, the solvent may be in the form of an aqueous solution. For the case in which the termite insecticide active ingredient is present in the form of a capsule such as microcapsule, the solvent is preferably one capable of dissolving the capsule portion, but is not limited thereto. That is, the solvent is preferably one which can be used regardless of the form of the termite insecticide active ingredient. Methanol has a high ability to solubilize the termite insecticide active ingredient and is excellent in respect of high extraction efficiency. It is also excellent in respect of low hydrophobicity and less denaturation action on protein etc. 40 to 50% methanol is more excellent in respect of achievement of higher extraction efficiency and less hazardous nature. When the termite insecticide active ingredient is present in the form of a capsule such as microcapsule in soil, any of the above solvents can be used, but the capsule component should be completely dissolved, and the solvent in this case is preferably ethanol or dimethyl sulfoxide. Particularly, ethanol is preferable because it is relatively less toxic and commercially available anhydrous ethanol can be used to make easier measurement feasible.

(2) Antigen-Antibody Reaction Unit (a) Preparation of Immune Reaction Container in which the Identifying Antigen was Encapsulated (a-1) Preparation of the Identifying Antigen The identifying antigen competing with the termite insecticide active ingredient for the antigen-antibody reaction is the termite insecticide active ingredient or a derivative to which an enzyme was bound, so the derivative used is preferably one having a group binding to the enzyme. The usable enzyme is a known enzyme including, but not limited to, peroxidase, alkali phosphatase and β-galactosidase. For bonding the enzyme to the derivative, any methods can be used without particular limitation, under conditions where the enzyme is not inactivated. Hereinafter, structures of fipronil derivatives and imidacloprid derivatives are specifically described as examples of the termite insecticide active ingredients, but the present invention is not limited thereto.

The fipronil derivatives can include compounds represented by the following formula (3):

[Formula 3]

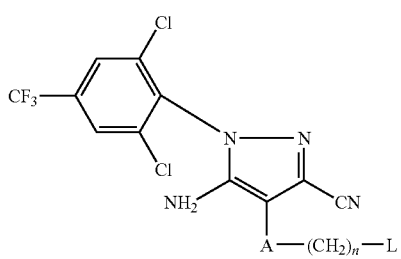

wherein A represent a member selected from the group consisting of —S(O)$_m$—, an oxygen atom, —CH$_2$— and —NH—, L represents a member selected from the group consisting of a carboxyl group, an amino group, an aldehyde group and a hydroxyl group, m is an integer selected from 0 to 2 and n is an integer selected from 1 to 10.

In the compound represented by the formula (3), L is covalently bound to a target macromolecule thereby forming a conjugate.

Production of the compound represented by the formula (3) used as hapten compound can be carried out by a known synthesis method and is not particularly limited, and for example, for the compound represented by the formula (3) wherein A is sulfur and L is a carboxyl group, a method shown the following reaction:

[Formula 4]

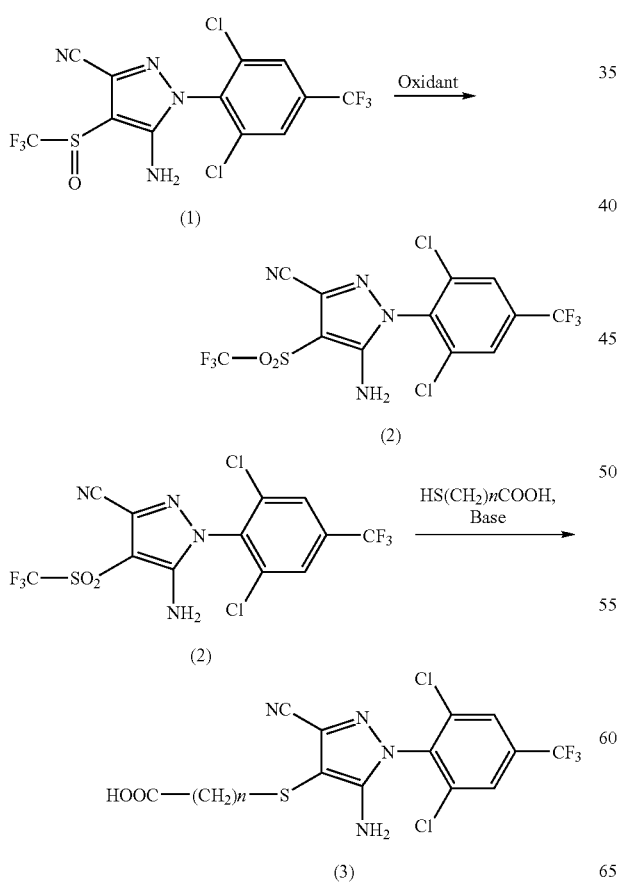

wherein n has the same meaning as defined above, is preferably used because the compound can be obtained in high yield in each step.

Specifically, in the above reaction formula:

(1) Step 1

5-amino-4-trifluoromethylsulfonyl-1-(2,6-dichloro-4-trifluoromethylphenyl) pyrazol-3-carbonitrile (1) is used as the starting material and reacted with an oxidizing agent to give 5-amino-4-trifluoromethylsulfonyl-1-(2,6-dichloro-4-trifluoromethylphenyl) pyrazol-3-carbonitrile (2) is obtained.

For example, the oxidizing agent which can be used in this reaction includes, but is not limited to, peracids such as hydrogen peroxide, peracetic acid, perbenzoic acid and m-chloroperbenzoic acid, ozone, potassium permanganate, and chromic acid. As the catalyst, tungsten and vanadium can also be used. The solvent includes, for example, alcohols such as methanol and ethanol, aromatic hydrocarbons such as benzene and toluene, ethers such as diethyl ether, dipropyl ether and tetrahydrofuran, ketones such as acetone and methyl ethyl ketone, nitrites such as acetonitrile and propionitrile, acid amides such as dimethylformamide and dimethyl acetamide, sulfoxides such as dimethyl sulfoxide, acids such as acetic acid, water and mixed solvents thereof. The reaction is carried out usually at room temperature to the boiling point of the solvent for about 30 minutes to 10 hours.

(2) Step 2

The resulting compound is reacted, in the presence of a base, with 3-mercaptoalkylcarboxylic acid to give ω-[5-amino-3-cyano-1-(2,6-dichloro-4-trifluoromethylphenyl) pyrazol-4-ylthio]alkylcarboxylic acid (3).

The base and solvent used in this reaction can be the same as in step 1. The reaction is carried out usually at 0° C. to the boiling point of the solvent for about 30 minutes to 10 hours.

Now, the structure of the imidacloprid derivative is described in detail.

The imidacloprid derivatives can include compounds represented by the following formula (5):

[Formula 5]

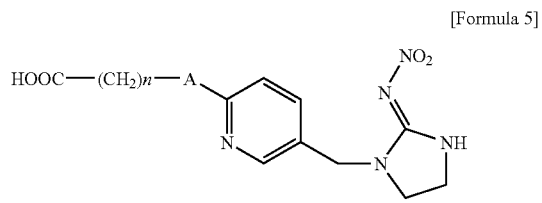

wherein A represent a member selected from the group consisting of S, O, CH$_2$ and NH, and n is an integer selected from 1 to 10.

In the compound represented by the formula (5), the carboxyl group is covalently bound to a target macromolecule thereby forming a conjugate.

Production of the compound represented by the formula (5) used as hapten compound can be carried out by a known synthetic method and is not particularly limited, and for example, the following method can be used.

First, a compound having a structure represented by the following formula (X1):

[Formula 6]

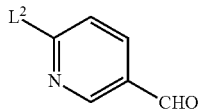
(X1)

wherein $L^2$ is a halogen atom selected from the group consisting of Cl, Br, and I, is reacted, in the presence of a base in an organic solvent, with a compound having a structure represented by the following formula (X2):

[Formula 7]

POOC—$(CH_2)_n$-AH  (X2)

wherein P is a carboxyl group-protecting group, and A and n have the same meanings as defined above, to give a compound having a structure represented by the following formula (X3):

[Formula 8]

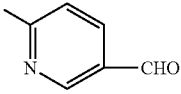
(X3)

wherein A, P and n have the same meanings as defined above.

The carboxyl group-protecting group represented by P may be a known protective group, and specific examples include a methyl group, ethyl group, tert-butyl group, benzyl group, p-methoxybenzyl group, 3,4-dimethoxybenzyl group, trichloroethyl group, trimethylsilyl group, tert-butyldimethylsilyl group, tert-butyldiphenylsilyl group, triethylsilyl group, triisopropylsilyl group, and trimethylsilylethyl group.

The reaction is carried out at a temperature of 0° C. to the boiling point of the solvent, preferably 10° C. to 100° C., for 5 minutes to 10 hours, preferably 30 minutes to 2 hours.

The solvent that can be used includes, for example, methanol, ethanol, benzene, toluene, xylene, dichloromethane, chloroform, carbon tetrachloride, diethyl ether, tetrahydrofuran, dioxane, acetone, methyl ethyl ketone, acetonitrile, ethyl acetate, dimethylformamide, dimethyl sulfoxide and water. The base includes sodium carbonate, potassium carbonate, sodium hydroxide, potassium hydroxide, sodium methylate, and sodium ethylate.

Then, the compound of the formula (X3) is reduced to give a compound having a structure represented by the following formula (X4):

[Formula 9]

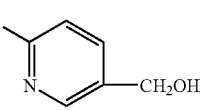
(X4)

wherein A, P and n have the same meanings as defined above.

The reductive reaction can be carried out by a known method. For example, the reductive reaction is carried out with a reducing agent such as sodium borohydride, aluminum lithium hydride etc. in a solvent such as methanol, ethanol, benzene, toluene, xylene, diethyl ether, tetrahydrofuran, dioxane, acetonitrile, ethyl acetate, acetic acid and water. The reaction is carried out under stirring at a temperature of −80° C. to the boiling point of the solvent, preferably 0° C. to 50° C., for 5 minutes to 10 hours, preferably 30 minutes to 5 hours.

Then, the compound of the formula (X4) is reacted with a halogenating agent such as thionyl chloride in an organic solvent such as chloroform, dichloromethane etc. or by using the halogenating agent as the solvent, to give a compound having a structure represented by the following structure (X5):

[Formula 10]

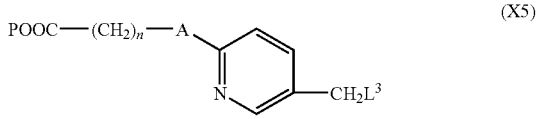
(X5)

wherein $L^3$ is a halogen atom selected from the group consisting of Cl, Br and I, and A, P and n have the same meanings as defined above.

The reaction is carried out at a temperature of 0° C. to the boiling point of the solvent, preferably room temperature to 100° C., for 5 minutes to 10 hours, preferably 30 minutes to 3 hours.

Then, the compound of the formula (X5) is reacted, in the presence of a base in an organic solvent, with 2-nitroiminoimidazolidine having a structure represented by the following formula (X6):

[Formula 11]

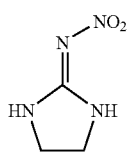
(X6)

thereby giving a compound having a structure represented by the following formula (X7):

[Formula 12]

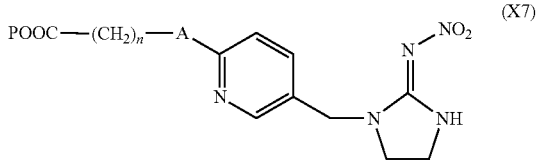
(X7)

wherein A, P and n have the same meanings as defined above.

The reaction is carried out at a temperature of 0° C. to the boiling point of the solvent, preferably room temperature to 100° C., for 5 minutes to 10 hours, preferably 30 minutes to 3 hours.

The solvent and base for synthesis of the compound of the formula (X7) can be the same as in used in synthesis of the compound of the formula (X3).

By further removing a carboxyl group-protecting group represented by P from the compound of the formula (X7), the compound of the formula (5) can be obtained. Removal of the carboxyl group-protecting group can be carried out by known methods such as alkali hydrolysis, acid hydrolysis etc.

In the case of acid hydrolysis, the compound of the formula (5) can be obtained by dissolving the compound of the formula (X7), preferably in an organic solvent such as acetic acid, formic acid, benzene, dichloromethane, 1,2-dichloroethane etc., then adding hydrochloric acid, sulfuric acid, a boron trifluoride/diethyl ether complex, trifluoroacetic acid, trifluoromethanesulfonic acid, p-toluenesulfonic acid etc., and reacting the mixture under stirring at a temperature of 0° C. to the boiling point of the solvent, preferably 0° C. to 50° C., for 5 minutes to 10 hours, preferably 1 hour to 5 hours.

In the case of alkali hydrolysis, the compound of the formula (5) can be obtained by dissolving the compound of the formula (X7), preferably in an organic solvent such as methanol, ethanol, tetrahydrofuran, ethylene glycol etc., then adding an aqueous of sodium hydrogen carbonate, sodium carbonate, potassium carbonate, lithium hydroxide, sodium hydroxide or potassium hydroxide, and reacting the mixture under stirring at a temperature of 0° C. to the boiling point of the solvent, preferably 0° C. to room temperature, for 5 minutes to 10 hours, preferably 1 hour to 2 hours.

When P is a benzyl group, its removal can also be carried out by hydrogenolysis with hydrogen.

When P is a silyl atom-containing group, its deprotection can also be carried out with a fluorine anion-generating reagent such as tetra-n-butyl ammonium fluoride, pyridinium fluoride or the like.

The compound obtained by the production method described above can be subjected if necessary to silica gel chromatography or recrystallization, to give a purified product of higher purity.

(a-2) Immune Reaction Container

The immune reaction container used is preferably a container made of glass or resin such as polypropylene and polyethylene as illustrated in FIGS. 1(A), (B), (C) and (D). This reaction container preferably has a structure to which a sealing member having an antibody immobilized thereon can be fit, but is not limited thereto.

(a-3) Encapsulation of the Identifying Antigen in the Immune Reaction Container

The above reaction container preferably employs a combination of at least one reaction container in which an identifying antigen has been previously encapsulated and at least one reaction container in which an identifying antigen and a termite insecticide effective ingredient of known amount have been previously encapsulated. In the present invention, the concentration of an effective ingredient in a sample is detected as a change in color density after coloration reaction, so it is preferable that the concentration is judged by comparison with a standard clarified for a change in coloration such as color density in background state or reaction result by an active ingredient of known concentration.

Specifically, an active ingredient-containing sample solution is introduced into one reaction container in which the identifying antigen has been previously encapsulated, and this reaction container is compared with a reaction container in which one or more identifying antigens and an active ingredient of known amount (in the case of two or more active ingredients, different known amounts are preferable), and from the relationship with the active ingredient of known amount as standard, the concentration of the active ingredient in the sample solution can be measured.

The identifying antigen encapsulated in the reaction container is preferably encapsulated in a previously lyophilized state. The biological molecule constituting the identifying antigen described above hardly maintains its activity and is often denatured in a short time particularly in the coexistence of water. In the present invention, the identifying antigen is encapsulated in a previously lyophilized state, whereby the biological molecule can be prevented from being denatured until actual use. Specifically, an aqueous solution of the identifying antigen is added to the reaction container and frozen in a space at about −20° C. to −100° C. and lyophilized by drying it in a frozen state in vacuum, whereby it can be stably encapsulated.

Besides lyophilization of the identifying antigen only, the identifying antigen and a termite insecticide active ingredient of known amount may be mixed and lyophilized. By adding a sample solution or a dissolving liquid on site, dissolution and reaction can be simultaneously initiated.

In addition to the reaction container in which a standard mixture of the identifying antigen and the termite insecticide active ingredient of known amount was encapsulated, a reaction container to which the termite insecticide active ingredient was not introduced for measuring the background is used as a comparative control for improving measurement accuracy, whereby the concentration of the termite insecticide active ingredient in the sample solution can be measured highly accurately.

Alternatively, when the concentration of the termite insecticide active ingredient in the sample can be predicted, a reaction container in which the termite insecticide active ingredient of known concentration around the predicted concentration is prepared for comparison, whereby the concentration of the termite insecticide active ingredient in the sample solution can be measured more accurately. Alternatively, the number of reaction containers in which the termite insecticide active ingredient of known amounts were encapsulated is increased, and by comparison with a plurality of reference points, the concentration of the termite insecticide active ingredient can be measured more accurately even if the concentration of the termite insecticide active ingredient in the sample is unclear.

As described above, the identifying antigen only can be encapsulated in a lyophilized state in the reaction container, and in the reaction container, the identifying antigen can be dissolved with a diluted sample solution or a standard solution having the termite insecticide active ingredient of known amount. In this method, dissolution and reaction can be simultaneously initiated on site by introducing and stirring the solution.

(b) Preparation of a Fixing Member on which an Antibody is Immobilized (b-1) Preparation of Antibody A hapten compound derived from an active ingredient of a termite insecticide is conjugated with a high-molecular compound (protein) such as bovine serum albumin (BSA), rabbit serum albumin (RSA), ovalbumin (OVA), keyhole limpet hemocyanine (KLH), thyroglobulin (TG) or immunoglobulin and then used as antigen.

The method of forming the conjugate can be a known method and is not particularly limited. For example, a carboxy group of a hapten compound of fipronil or a hapten compound of imidacloprid can be reacted with a functional group of the polymer compound, to form a conjugate.

The antibody used in the present invention can be a polyclonal antibody obtained by separating and purifying an antibody contained in blood in a rabbit or goat immunized with the termite insecticide active ingredient or a monoclonal antibody obtained by separating and purifying an antibody secreted from a cloned hybridoma having an ability to produce an antibody. In the present invention, both the antibodies can be used, but because the monoclonal antibody is highly selective for an antigen, the monoclonal antibody is particularly preferable. The method of preparing the monoclonal antibody is not limited insofar as it is a known method. For example, the monoclonal antibody secreted in ascites fluid generated by inoculation of a mouse abdominal cavity with the hybridoma can be purified by a protein A column etc.

(b-2) Fixing Member

The fixing member refers to a member having a part, e.g., in the form of a bar, made of resin such as polyethylene/polystyrene to which a protein easily adheres, and preferably has an antibody-immobilized part easily contacted with a solution and having a large surface area.

The fixing member having a part on which the antibody was immobilized preferably has such a structure that it can be bound to a sealing member and introduced into and fit to a reaction container. Specifically, the unit preferably has a lid-shaped part (sealing member) 1 capable of fitting as shown in FIG. 1(A) and a stick-shaped part (fixing member) 2, wherein the antibody is immobilized in the top 3 of the stick-shaped part 2. Particularly, a large surface area can also be secured by forming the top 3 in penniform. The member having the antibody thus immobilized thereon can be combined with an immune reaction container 4. When the identifying antigen was encapsulated in the reaction container 4 and lyophilized so as not to contact with the sealing member, the lid-shaped part 1 and the stick-shaped part 2 can be sealed while being inserted in an integrated state into the reaction container.

The lid-shaped part 1 of the sealing member and the stick-shaped part 2 may be constituted to be detachable from each other. In the state before use, the immune reaction container is sealed with the lid-shaped part 1, and at the time of antigen-antibody reaction, the stick-shaped part 2 is fit to the lid-shaped part 1 and inserted into the reaction container, followed by sealing with the lid-shaped part 1. By this operation, the immune reaction container can be stirred to promote the reaction.

As shown in FIG. 1(B), the sealing member can be constituted such that the reaction container 4 is sealed merely with the lid-shaped part 1. Before antigen-antibody reaction, for example the lyophilized identifying antigen is sealed to secure the stability of the identifying antigen, and at the time of reaction, carrier such as latex beads 5, is encapsulated as antibody-fixing member in the reaction container 4 followed by sealing thereby enabling stirring to promote the reaction. In this case, the antibody is not directly immobilized on the sealing member, and the bead carrier separated from the sealing member is used as the antibody-fixing member.

(b-3) Immobilization of the Antibody onto the Fixing Member

In immobilization of the antibody, for example a buffer solution containing the antibody may be placed on the sealing member and incubated thereon. The concentration of the antibody in the buffer solution is usually about 0.01 µg/mL to 10 µg/mL. The buffer solution is not particularly limited and may be a conventional buffer solution.

Hereinafter, the fixing member having the antibody immobilized thereon is referred to as "antibody-immobilized carrier."

(b-4) Blocking of the Surface of the Carrier

To prevent unspecific adsorption of contaminants in a sample onto the surface of the carrier thereby preventing them from influencing the reaction, the surface of the carrier on which the antibody was not immobilized is preferably blocked with a protein or the like not reactive with the antibody or the identifying antigen. As the blocking agent, a solution of bovine serum albumin (BSA) or skim milk, or commercially available Block Ace (manufactured by Dainippon Sumitomo Pharmaceutical Co., Ltd.), can be used. Blocking is carried out by contacting the antibody-immobilized carrier with an excess of a blocking solution, incubating it for example at about 4° C. overnight and washing it with a wash fluid. The wash fluid is not limited, and for example, a buffer solution containing sodium chloride at the physiological saline concentration can be used.

(b-5) Stabilization of the Blocked Fixing Member

The blocked fixing member having the antibody immobilized thereon can be stabilized by drying. Drying is preferably conducted at low temperatures by any of drying methods such as vacuum-lyophilization, drying under reduced pressure, and air drying.

(c) Antigen-Antibody Reaction

A sample prepared in the extraction unit is provided to the antigen-antibody reaction unit. Specifically, the sample is added to the immune reaction container having the identifying antibody encapsulated therein, and then the fixing member having the antibody immobilized thereon is inserted thereby initiating the antigen-antibody reaction. In this step, the reaction container can be sealed with the sealing member bound to the inserted fixing member. By further adding a solution without containing the termite insecticide active ingredient to the immune reaction container in which the termite insecticide active ingredient of known concentration and the identifying antigen were encapsulated or to the immune reaction container in which the identifying antigen only was encapsulated, the concentration of the termite insecticide active ingredient in the sample can be examined more accurately. The antigen-antibody reaction is carried preferably at a reaction temperature of 4° C. to 37° C. for a reaction time of about 5 minutes to 2 hours.

(3) Detection Unit

After the reaction is finished, the reaction container, the fixing member and the sealing member are washed with tap water, purified water, a buffer solution etc., and then a substrate solution to be colored with an enzyme of the identifying antigen bound to the immobilized antibody is added to the reaction container. The coloring substrate is not particularly limited insofar as it is a known substrate, and 3,3',5,5'-tetramethylbenzidine may be used in the case of an enzyme such as peroxidase. By detecting a change in coloration occurring after addition of the substrate solution, the concentration of the termite insecticide active ingredient is judged.

Judgment of the concentration is carried out easily with the visual observation by comparing the degree of coloration with the termite insecticide active ingredient of known concentration. For more accurate measurement, the degree of coloration can be numerically expressed by a spectrophotometer.

Because it is desired that the termite insecticide can be measured on the site where it was applied, there is demand for a measurement method which can be easily carried out on site. In the present invention with the objective of providing an easy measurement method or measurement kit excellent in operativeness, not only qualitative measurement but also quantitative measurement at the level of ppb order can be secured by detecting a change in coloration with the visual observation for example on the basis of the color of the surface of the antibody-immobilized carrier.

By comparing a change in the coloration of the sample solution with a change in the coloration of the termite insecticide active ingredient solution of known concentration, quantification accuracy can be improved, and by comparison with changes in coloration of a plurality of termite insecticide active ingredient solutions of known concentrations, quantification accuracy can be further improved.

In a specific means for effective visual judgment, the reaction container may be a transparent reaction container 4, and as shown in FIG. 1(C), a white member 6 is added to the inner surface of half periphery of the reaction container 4, or as shown in FIG. 1(D), to the outer surface of the reaction container 4. Alternatively, as shown in FIG. 1(A), the antibody-immobilized part (stick-shaped part 2) of the sealing member can be a white member and the reaction container can be a transparent reaction container 4. By the above mentioned means, the coloration can be easily judged even with the visual observation. Since color density may vary with time or depending on temperature, measurement can be effected with higher accuracy particularly by comparison with a plurality of reaction containers in which termite insecticide active ingredients of known concentrations are encapsulated. On-site measurement is also feasible and is excellent in operativeness.

Using a spectrophotometer or the like as a detection means, the change in coloration can be numerically quantified. For example, when o-phenylene diamine (referred to hereinafter as "OPD") is used as the coloration substrate, the absorbance at 490 nm is measured. Other coloration substrate such as 3,3',5,5'-tetramethyl benzidine can also be used. In this case, the absorbance at 650 nm is measured. After the reaction is terminated with 0.5 M sulfuric acid or the like, the absorbance at 450 nm may be measured. When alkali phosphatase is used, there is a method of measuring by using e.g. p-nitrophenylphosphoric acid as coloring substrate. In any of the coloring methods, the concentration of the termite insecticide active ingredient in the sample solution can be quantified from a calibration curve prepared from the relationship between the concentration and absorbance of a reaction solution to which the termite insecticide active ingredient of known concentration was added.

The termite insecticide active ingredient can also be measured by an immunoassay method in which the identifying marker of the identifying antigen is replaced by color latex or gold colloid, other than the enzyme immunoassay method. Such identifying antigen can be prepared by binding a protein such as albumin to the termite insecticide active ingredient or to its derivative and immobilizing the resulting protein conjugate with the surface of color latex or gold colloid by a method known in the art. The prepared identifying antigen can be encapsulated in the immune reaction container in the same manner as in application to ELISA described above, and the termite insecticide active ingredient can be measured by subjecting the antibody to antigen-antibody reaction with the antibody-immobilized fixing member. In the case of these immunoassay methods, the subsequent coloration procedure is not necessary and during the antigen-antibody reaction, color latex or gold colloid is colored by being bound to the immobilized antibody on the surface of the fixing member. The degree of coloration is judged with the visual observation, whereby the concentration of the termite insecticide active ingredient can be measured.

The measurement kit of the present invention can arbitrarily include a dilution unit for diluting, to a predetermined ratio, the sample solution prepared in the extraction unit. The dilution unit is preferable as a means for dilution in the optimum concentration range because measurement in the solvent at high concentration by ELISA is difficult. The diluting fluid is preferably water. For example, when 100% methanol or 100% ethanol is used in extraction in the extraction unit, the degree of dilution is preferably about 2 to 20-fold, and the final concentration is preferably about 5 to 50%.

<Example of the Measurement Kit of the Present Invention>

In a specific example of the measurement kit for measuring the termite insecticide active ingredient in soil, the following apparatus can also be produced. First, an extraction unit having an injection part for adding a predetermined amount of solvent is arranged. Soil as the measurement object can be introduced into this extraction unit, and a solvent can be added through the injection part. The measurement kit further includes a transfer means such as a tube pump for transferring a termite insecticide active ingredient-containing sample solution from the extraction unit; a reaction unit having an identifying antigen and a fixing member on which an anti-termite insecticide active ingredient antibody reacting with a termite insecticide active ingredient-containing sample solution are immobilized; and a detection unit for detecting a change in coloration of the sample solution subjected to antigen-antibody reaction in the reaction unit.

In this apparatus, a solvent may be automatically injected upon introduction of a predetermined amount of soil. Alternatively, a solvent may be added separately. Thereafter, the mixture is stirred etc. in the extraction unit, whereby the termite insecticide active ingredient is extracted. A supernatant of such extract is sent to the reaction unit by a transfer means, and in the reaction unit, a solution undergoing the antigen-antibody reaction is produced. By measuring the absorbance of the reaction solution, the termite insecticide active ingredient in soil can be quantified.

Hereinafter, specific examples of the measurement kit and measurement method are described in more detail by reference to the Examples, but the present invention is not limited thereto.

EXAMPLE 1

Preparation of Antigen and Antibody with Respect to Fipronil (1) Synthesis of 5-amino-1-(2,6-dichloro-4-(trifluoromethyl)phenyl)-4-(((trifluoromethyl)sulfonyl)-1H-pyrazol-3-carbonitrile 0.17 g (0.4 mmol) of 5-amino-1-(2,6-dichloro-4-(trifluoromethyl) phenyl)-4-((trifluoromethyl) sulfinyl)-1H-pyrazol-3-carbonitrile, 0.01 g (0.03 mmol) of sodium tungstate.2H$_2$O, and 0.07 g (0.6 mmol) of 30% aqueous hydrogen peroxide were dissolved in 1 mL acetic acid and reacted at 55° C. for 6 hours. The reaction solution was cooled, 10 mL water was added, and the reaction mixture was extracted twice with 10 mL ethyl acetate. The ethyl acetate layer was washed with water, then dehydrated over anhydrous magnesium sulfate, filtered and concentrated to give 0.2 g pale yellow crystal of 5-amino-1-(2,6-dichloro-4-(trifluoromethyl) phenyl)-4-((trifluoromethyl) sulfonyl)-1H-pyrazol-3-carbonitrile.

(2) Synthesis of 3-[5-amino-3-cyano-1-(2,6-dichloro-4-trifloromethylphenyl)-1H-pyrazol-4-ylthio]propionic acid 0.15 g (0.33 mmol) of 5-amino-1-(2,6-dichloro-4-(trifluoromethyl)phenyl)-4-((trifluoromethyl) sulfonyl)-1H-pyrazol-3-carbonitrile was dissolved in 4 mL of ethanol, and 0.04 g (0.36 mmol) of 3-mercaptopropionic acid and 0.1 g (0.69 mmol) of potassium carbonate were added thereto and heated at 70° C. for 1 hour and then refluxed for 4 hours. After the solvent was distilled away from the reaction mixture, water was added thereto, the pH was adjusted to 3 with 1 N hydrochloric acid, and the reaction product was extracted twice with ethyl acetate. The ethyl acetate layer was dehydrated over anhydrous magnesium sulfate, then filtered, concentrated and purified through a silica gel column (hexane:ethyl acetate=70:30) to give 0.12 g (yield 85.3%) of pale yellow crystal of 3-[5-amino-3-cyano-1-(2,6-dichloro-4-triflorom-ethylphenyl)-1H-pyrazol-4-ylthio]propionic acid.

$^1$H NMR (DMSO-$d_6$) δ 2.56 (2H, m, $CH_2$), 3.29 (2H, m, $CH_2$), 7.85 (2H, s, $NH_2$), 7.90 (1H, s, $CH_2$), 8.01 (1H, s, CH), 12.4 (1H, s, COOH)

(3) Preparation of Immunogen

As immunogen, a conjugate of bovine serum albumin (BSA) and the fipronil hapten in the above (2) was prepared by an active ester method.

2.1 mg of 3-[5-amino-3-cyano-1-(2,6-dichloro-4-triflo-romethylphenyl)-1H-pyrazol-4-ylthio]propionic acid (fipronil hapten) prepared in (2), 1.2 mg of N-hydroxysuccin-imide and 1.9 mg of 1-ethyl-3-(3-dimethylaminopropyl)-carbodiimide hydrochloride were dissolved in 200 µL of N,N-dimethylformamide, and the resulting solution was allowed to stand in the dark place at 25° C. for 1.5 hours to give a fipronil hapten solution.

Separately, 10 mg BSA was added to 1 mL of 0.1 M borate buffer solution (pH 8.0) and stirred overnight to give a BSA solution.

The previously prepared fipronil hapten solution was added dropwise to the BSA solution and stirred in the dark place at room temperature for 1.5 hours. After the reaction was finished, the reaction mixture was dialyzed against a physiological phosphate buffer solution (PBS, 10 mM phosphate buffer solution, 150 mM NaCl, pH 7.0) at 4° C. for 2 days and then stored at −40° C. A conjugate of fipronil hapten and BSA thus obtained was used as immunogen.

(4) Preparation of a Monoclonal Antibody-Producing Hybridoma

The immunogen prepared in (3) was dissolved at 2 mg/mL in PBS, mixed with an equal volume of complete adjuvant (trade name: Freund's complete adjuvant; FCA) and then emulsified, and 100 µL of the resulting emulsion was administered intraperitoneally to a 6- to 7-week-old female BALB/C mouse. In a similar manner, 100 µL of 0.5 mg/mL immunogen mixed with an equal volume of incomplete adjuvant (trade name: Freund's incomplete adjuvant: FICA) was administered as booster at 2-week intervals. After immunization was conducted 4 times, blood was collected from eye ground, and the antibody titer in serum was confirmed by the indirect competitive method. The titer was confirmed to be sufficiently increased, and 1 week thereafter, 10 µg immunogen/100 µL PBS was administered in final immunization through a caudal vein to the mouse. Three days thereafter, the spleen was excised from the mouse and subjected to cell fusion.

After a superfluous tissue section was removed from the excised spleen in a serum-free DMEM medium (Dulbecco's modified Eagle medium), cells were removed completely from the spleen and suspended in the medium. To precipitate suspended large tissue sections, the sample was left for 5 minutes, and the cell suspension was collected in a centrifuge tube and centrifuged at 1500 rpm, and the supernatant was removed by suction, and a fresh serum-free DMEM was added to it to suspend the cells. This operation was carried out twice.

Previously cultured myeloma cells (P3X63Ag8.653) were recovered, centrifuged to remove a supernatant, and suspended repeatedly twice in a serum-free DMEM medium.

The respective cells were counted and mixed such that the ratio of the spleen cells to the myeloma cells became 10:1 to 7.5:1, and the mixed cells were centrifuged at 1500 rpm for 5 minutes and the supernatant was removed by suction.

While the centrifuge tube was stirred vigorously, 2 mL of 50% polyethylene glycol (molecular weight 1500) was added over about 60 seconds. Then, about 10 mL serum-free DMEM was added over 3 to 4 minutes under stirring.

The centrifuge tube was centrifuged at 1000 rpm for 5 minutes to remove the supernatant completely, and the spleen cells were suspended at $2.5 \times 10^6$ cells/mL in HT medium (DMEM medium supplemented with hypoxanthine, thymidine and 10% fetal bovine serum) and pipetted in a volume of 100 µL/well to a 96-well culture plate, and culture was initiated at 37° C. in 8% carbon dioxide gas under humidified conditions.

On the next day, HAT medium (DMEM medium supplemented with hypoxanthine, thymidine, aminopterin, 10% fetal bovine serum) was added in a volume of about 40 µL/well, and the cells were observed until the myeloma cells perished and a colony of the hybridoma cells was formed, and thereafter, HT medium was added while the cells were continuously observed.

Ten days after culture was initiated, the culture was collected, and a well in which the antibody against fipronil had been produced was selected by the indirect competitive ELISA method and cultured in an increasing scale in 96 wells, 48 wells and 24 wells sequentially.

Cloning was carried out by limiting dilution in the 24-well stage, and a monoclonal antibody-producing hybridoma strain (FPN-1E9-25) against fipronil was obtained. The resulting hybridoma strain has been deposited under Accession No. FERM AP-20384 since Feb. 2, 2005, with International Patent Organism Depositary (IPOD), National Institute of Advanced Industrial Science and Technology (AIST), Japan.

(5) Preparation of Monoclonal Antibody

The hybridoma strain obtained as described above was cultured in DMEM containing 10% fetal bovine serum, and about $2 \times 10^6$ cells were injected intraperitoneally to Balb/c female Retire mouse, and then the ascites fluid was collected. The resulting ascites fluid was applied onto a protein G column to purify IgG.

(6) Immobilization of the Antibody onto the Fixing Member

Fixation of the monoclonal antibody obtained in (5) to the fixing member was carried out by using an anti-mouse goat antibody as secondary antibody. A plate-shaped fixing member having a 5.2 $cm^2$ surface area (symbol 2 in FIG. 1) was added to 1.6 µg/ml secondary antibody solution and left at 4° C. overnight. Then, it was washed with 10 mM phosphate buffer (PBS) containing 150 mM NaCl. This plate-shaped fixing member was placed in PBS containing 0.4% Block Ace and left at 20° C. for 1 hour. Further, the stick was placed in 5 g/ml monoclonal antibody solution obtained in (5) and left at 20° C. for 1 hour, followed by washing and drying. In the following examples, the immobilized antibody thus obtained was used.

EXAMPLE 2

Preparation of Antigen and Antibody with Respect to Imidacloprid

Synthesis of ethyl 3-(5-formyl-2-pyridylthio) propionate (1)

1.4 g (10 mmol) of 2-chloro-5-formyl pyridine, 1.5 g (11 mmol) of ethyl thioglycolate and 1.6 g (11.5 mmol) of potassium carbonate were added to 20 ml ethanol, and this mixture was stirred for 1 hour under reflux. The reaction mixture was concentrated, and 30 ml water was added to the resulting residues which were then extracted twice with 70 ml ethyl acetate. The ethyl acetate layer was washed with water, dried over anhydrous magnesium sulfate and concentrated. The resulting residues were purified by silica gel chromatography (n-hexane ethyl acetate=2:1) to give 1.7 g of (1) (yield 71%).

Synthesis of ethyl 3-(5-hydroxymethyl-2-pyridylthio) propionate (2)

A solution of 0.32 g (8.4 mmol) sodium borohydride in 3 ml of water was added at 10 to 15° C. to a solution of 2.0 g (8.4 mmol) of ethyl 3-(5-formyl-2-pyridylthio) propionate in 20 ml of 1,4-dioxane, and the mixture was stirred at room temperature for 30 minutes. The reaction mixture was concentrated, 40 ml of water was added to the resulting residues which were then extracted twice with 70 ml of ethyl acetate. The ethyl acetate layer was washed with water, dried over anhydrous magnesium sulfate and concentrated. The resulting residues were purified by silica gel chromatography (n-hexane:ethyl acetate=2:1, then ethyl acetate:methanol=1:1) to give 1.4 g of (2) (yield 70%).

Synthesis of ethyl 3-(5-chloromethyl-2-pyridylthio) propionate (3)

2.2 g (9.0 mmol) of ethyl 3-(5-hydroxymethyl-2-pyridylthio) propionate (2) was dissolved in 5 ml of chloroform, and 1.3 g (11 mmol) of thionyl chloride was added at 10 to 15° C. to this solution and stirred at room temperature for 1 hour. The reaction mixture was concentrated, and 25 ml of 5% aqueous sodium bicarbonate was added to the resulting residues which were then extracted twice with 70 ml of ethyl acetate. The ethyl acetate layer was washed with water, dried over anhydrous magnesium sulfate and concentrated. The resulting residues were purified by silica gel chromatography (n-hexane:ethyl acetate=2:1) to give 2.3 g of (3) (yield 64%).

Synthesis of ethyl 3-[5-(2-nitroiminoimidazolidin-1-ylmethyl)-2-pyridylthio]propionate (4)

0.8 g (6.2 mmol) of 2-nitroiminoimidazolidine, 1.6 g (6.2 mmol) of ethyl 3-(5-chloromethyl-2-pyridylthio) propionate and 0.94 g (6.8 mmol) of potassium carbonate were added to 10 ml acetonitrile, and this mixture was stirred for 2 hours under reflux. The reaction mixture was concentrated, and 30 ml of water was added to the resulting residues which were then extracted twice with 70 ml of ethyl acetate. The ethyl acetate layer was washed with water, dried over anhydrous magnesium sulfate and concentrated. The resulting residues were purified by silica gel chromatography (ethyl acetate) to give 1.5 g of (4) (yield 68%).

Synthesis of 3-[5-(2-nitroiminoimidazolidin-1-ylmethyl)-2-pyridylthio]propionic acid (5)

0.44 g (11 mmol) of sodium hydroxide dissolved in 30 ml water was added to a suspension containing 1.3 g (3.7 mmol) of ethyl 3-[5-(2-nitroiminoimidazolidin-1-ylmethyl)-2-pyridylthio]propionate (4) in 40 ml of ethanol and stirred at room temperature for 1 hour. The ethanol was distilled away under reduced pressure, and 20 ml of water and 30 ml of ether were added to the residues which were then partitioned, and the aqueous layer was adjusted to pH 5 with dilute hydrochloric acid and extracted twice with 70 ml of ethyl acetate. The ethyl acetate layer was washed with water, dried over anhydrous magnesium sulfate and concentrated. The residues were purified by silica gel chromatography (ethyl acetate: methanol=1:1) to give 0.6 g of (5) (yield 50%).

Physical property data on the imidacloprid hapten (5) by $^1$H-NMR (chemical shift δ)

$^1$H-NMR (DMSO-D6, 400 MHz) δ 2.62 (2H, m, $CH_2$), 3.29 (2H, m, $CH_2$), 3.47 (2H, m, $2H_2$), 3.62 (2H, m, $CH_2$), 4.42 (2H, s, $CH_2$), 7.31 (1H, m, Pyr: H), 7.58 (1H, m, Pyr: H), 8.43 (1H, m, Pyr: H), 8.95 (1H, s, NH), 12 (1H, br, COOH)

(3) Preparation of Immunogen

A conjugate consisting of bovine serum albumin (BSA) conjugated with imidacloprid hapten of (2) above was prepared as immunogen by the active ester method.

0.2 mmol of the imidacloprid hapten prepared in (2) was dissolved in 1.0 mL of DMSO, and 0.3 mmol of N-hydroxysuccinic acid imide and 0.3 mmol of 1-ethyl-3-(3-dimethylaminopropyl) carbodiimide were added thereto and stirred at room temperature for 3.5 hours. After the reaction, the reaction mixture was centrifuged at 10000 rpm for 15 minutes to separate it into a supernatant and precipitates.

Separately, 50 mg of BSA was dissolved in 5.0 mL of 145 mM NaCl-0.01 M phosphate buffer solution (pH 7.2) (referred to hereinafter as PBS), and then 1.05 mL of DMSO was added to prepare a solution. To this solution was added 0.25 mL of the above supernatant, and the mixture was reacted at room temperature for 16 hours. After the reaction, the sample was dialyzed against distilled water at 4° C. to prepare a conjugate of the imidacloprid hapten and BSA (hereinafter referred to as imidacloprid hapten-BSA conjugate) which was thereafter used as antigen for immunization.

(4) Preparation of Monoclonal Antibody-Producing Hybridoma

For immune sensitization, Balb/c mouse was used. 100 μg of the imidacloprid hapten-BSA conjugate prepared in (3) was dissolved in 50 μL PBS and mixed with an equal volume of Freund's complete adjuvant and used in subcutaneously inoculating the Balb/c mouse. After 4 weeks, the antigen for immunization prepared in the same manner as above except for use of Freund's incomplete adjuvant was used as booster to immunize the mouse. In the sixth week, the mouse was immunized via the caudal vein with 30 μg antigen for immunization as booster dissolved in 180 μL PBS.

Subsequently, mouse spleen cells with an increase in the activity of anti-imidacloprid antibody in serum were fused with myeloma cells (Sp2/0-Ag14) by the polyethylene glycol method in accordance with the method of Shuji Yamashita (Histochemistry and Cytochemistry; edited by Japan Society of Histochemistry and Cytochemistry and published by Gakusai Kikaku, 1986) and cultured. Microplate was coated with the solution of imidacloprid hapten-BSA conjugate and then blocked by BlockAce (manufactured by Snow Brand Milk Product CO., Ltd., code No. VK-25B). To a coated and blocked plate was added 50 μL/well culture supernatant where cell proliferation was observed, followed by reaction at room temperature for 1 hour.

After washing 5 times with PBS, peroxidase-conjugated anti-mouse IgG goat antibody (manufactured by Tago) diluted 2000-fold with a 10-fold dilution of Block Ace was added in a volume of 50 μL/well, and reacted at room temperature for 1 hour. After washing 5 times with PBS, 0.1 M citric acid-phosphate buffer (pH 5.0) containing 2 mg/mL OPD and 0.02% hydrogen peroxide was added in a volume of 50 μL/well and then allowed to be colored at room temperature for 10 minutes.

Then, the reaction was terminated by adding 1 N sulfuric acid in a volume of 50 μL/well, and the absorbance at 490 nm was measured, and cells (hybridomas) showing reactivity were selected. Then, the reactivity of each well with imidacloprid was examined by the indirect competitive ELISA method shown in Example 4, and the cells producing the objective antibody was cloned by limiting dilution. As a result, several hybridoma strains were cloned as cells producing the anti-imidacloprid antibody. In the stage of 24 wells, cloning was carried out by limiting dilution, whereby a hybridoma strain [33C3-1-1] producing a monoclonal antibody against imidacloprid was obtained. The resulting hybridoma stain has been deposited under Accession No. FERM P-17094 since Dec. 17, 1998, with former Agency of Industrial Science and Technology, National Institute of Bioscience and Human-Technology.

(5) Preparation of Monoclonal Antibody

The hybridoma strain obtained above was cultured in DMEM containing 10% fetal bovine serum, and about 2×10$^6$ cells were injected intraperitoneally to a Balb/c female Retire mouse, and the ascites fluid was collected. The obtained ascites fluid was applied to a protein G column to purify IgG.

(6) Immobilization of the Antibody onto the Fixing Member

Fixation of the monoclonal antibody obtained in (5) to the fixing member was carried out by using an anti-mouse goat antibody as secondary antibody. A plate-shaped fixing member having a 5.2 cm$^2$ surface area (symbol 2 in FIG. 1) was added to 1.6 μg/ml secondary antibody solution and left at 4° C. overnight. Then, it was washed with 10 mM phosphate buffer (PBS) containing 150 mM NaCl. This plate-shaped fixing member was placed in PBS containing 0.4% BlockAce and left at 20° C. for 1 hour. Further, the stick was placed in 5 g/ml monoclonal antibody solution obtained in (5) and left at 20° C. for 1 hour, followed by washing and drying. In the following examples, the immobilized antibody thus obtained was used.

EXAMPLE 3

A fipronil measurement kit comprising a combination of measurement means consisting of the respective units, to which ELISA was applied, specifically comprises a reagent constitution as shown in Table 1. This measurement kit was used to verify the measurement range of fipronil.

TABLE 1

| Unit | Reagent constitution |
| --- | --- |
| Reaction unit (reaction container) | Lyophilized fipronil derivative conjugated with horseradish roxidase is contained. |
| Fixing member (antibody stick) | Anti-fipronil antibody is immobilized, blocked and then air-dried. |

TABLE 1-continued

| Unit | Reagent constitution |
| --- | --- |
| Detection unit (coloration reagent) | 3,3',5,5'-Tetramethylbenzidine solution is contained as coloration reagent. |

(1) Preparation of Standard Solutions

A fipronil standard reagent (manufactured by Wako Pure Chemical Industries, Ltd.) was dissolved in methanol and diluted with purified water to give 5% methanol solution from which standard dilution series of 0.0050, 0.010, 0.020, 0.080 and 0.20 ppm were prepared.

(2) Antigen-Antibody Reaction 1 mL of each standard solution was added to the reaction container, and the previously encapsulated identifying antigen was dissolved in, and mixed with, the standard solution. Immediately, the antibody stick was fit to the reaction container and the antigen-antibody reaction was carried out at 25° C. for 10 minutes.

(3) Detection of Change in Coloration

Figure 2:
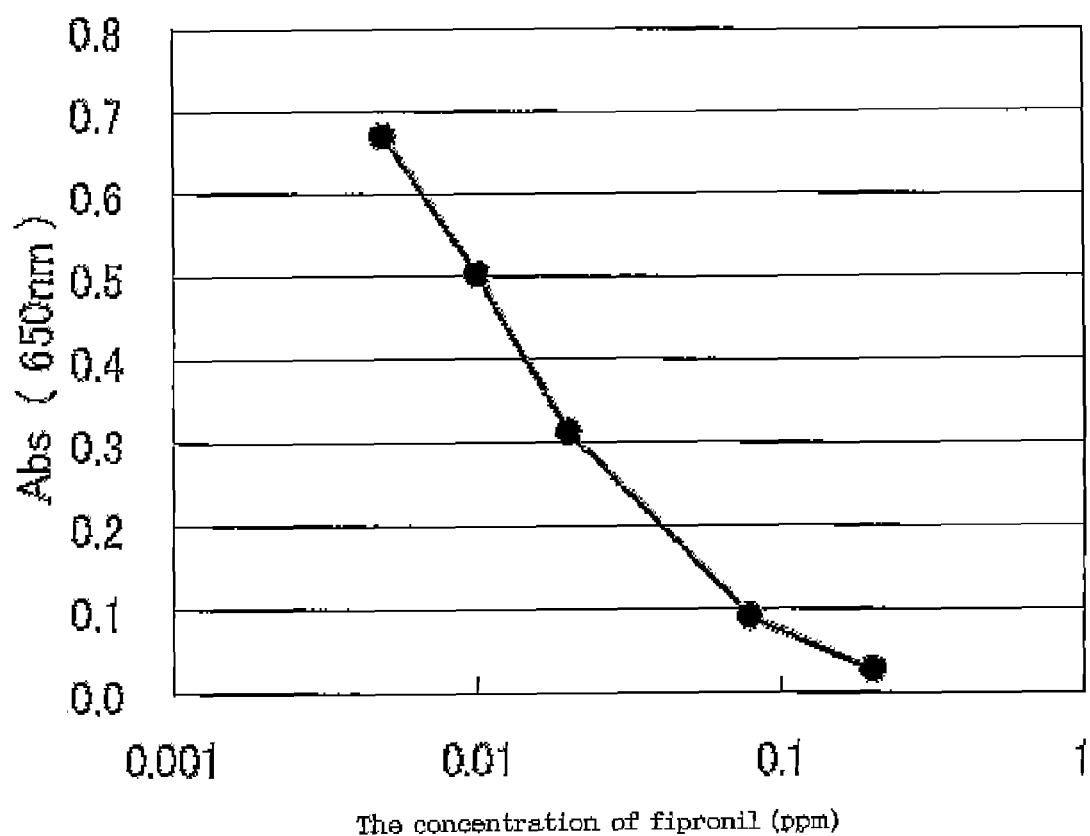
FIG. 2 is a standard curb resulting from a measurement of fipronil with the use of measurement kit of the present invention.

The reaction container and the antibody stick were washed with tap water to remove the identifying antigen not bound to the immobilized antibody. After the residual wash was sufficiently removed, the coloration reagent was added to the reaction container, and the antibody stick was fit thereto, followed by coloration reaction for 10 minutes to determine the absorbance at 650 nm. The result revealed that as shown in FIG. 2, fipronil can be measured at 0.0050 to 0.080 ppm in an almost linear standard curve. Accordingly, visual judgment is feasible in this measurement range.

EXAMPLE 4

Then, a specific example of the measurement kit and measurement method for measuring fipronil in soil is specifically described. A fipronil measurement kit comprising a combination of measurement means consisting of the respective units comprises a reagent constitution as shown in Table 2. Using this measurement kit, fipronil in soil was actually measured.

TABLE 2

| Unit | Reagent constitution |
| --- | --- |
| Extraction unit (extraction bottle) | 5 mL of 50% methanol is contained |
| Dissolving reagent | 5% methanol is contained |
| Reaction unit (reaction container) | Lyophilized fipronil derivative conjugated with horseradish peroxidase is contained |
| Fixing member (antibody stick) | Anti-fipronil antibody is immobilized, blocked and then air-dried. |
| Detection unit (coloration reagent) | 3,3',5,5'-Tetramethylbenzidine solution is contained as coloration reagent. |

(1) Preparation of Sample Solutions 1 g of sample soil (containing 1 ppm fipronil and 10% organic matter) was weighed out and transferred to the extraction container, and stirred for 1 minute in 5 mL of 50% methanol to extract fipronil contained therein. Tap water was added to the extraction container to give 50 mL of mixture, and its supernatant was used as a sample solution.

(2) Antigen-Antibody Reaction 1 mL of the sample solution or standard solution was added to the reaction container, and the previously encapsulated identifying antigen was dissolved in, and mixed with, the sample solution or standard solution. Immediately, the antibody stick was fit to the reaction container and the antigen-antibody reaction was carried out at 25° C. for 10 minutes.

(3) Detection of Change in Coloration

The reaction container and the antibody stick were washed with tap water to remove the identifying antigen not bound to the immobilized antibody. After the residual wash was sufficiently removed, the coloration reagent was added to the reaction container, and the antibody stick was fit thereto, followed by coloration reaction for 10 minutes to determine the absorbance at 650 nm.

The standard solution was used to prepare a calibration curve, and the concentration of fipronil recovered from the sample soil was determined. As a result, the concentration of fipronil in soil was accurately determined to be 1 ppm.

EXAMPLE 5

Then, a specific example of the measurement kit and measurement method for visually judging fipronil in soil is specifically described. A fipronil measurement kit comprising a combination of measurement means consisting of the respective units comprises a reagent constitution as shown in Table 3. The procedure of visually judging the concentration of fipronil in soil by using this measurement kit is described.

TABLE 3

| Unit and reagent constitution | Volume | Number |
|---|---|---|
| Extraction bottle (containing 5 mL of 50% methanol) | 50 mL | 1 bottle |
| Dissolving reagent (containing 5% methanol) | 3 mL | 1 bottle |
| Reaction container (containing lyophilized fipronil derivative conjugated with horseradish peroxidase) A: for negative control (0 ppm fipronil) B: for positive control (containing 0.020 ppm fipronil) C: for sample measurement | 1 mL for each | 1 container for each |
| Antibody stick (anti-fipronil antibody is immobilized, blocked and then air-dried) | — | 3 sticks |
| Coloration reagent (containing 3,3',5,5'-tetramethylbenzidine solution) | 4 mL | 1 bottle |

(1) Preparation of Sample Solutions 1 g of sample soil (containing 1 ppm fipronil and 10% organic matter) was weighed out and transferred to the extraction container, and stirred for 1 minute in 5 mL of 50% methanol to extract fipronil contained therein. Tap water was added to the extraction container to give 50 mL of mixture, and its supernatant was used as a sample solution.

(2) Antigen-Antibody Reaction 1 mL of dissolving reagent was added to the reaction containers A and B, and 1 mL of sample solution was added to the reaction container C, and the previously encapsulated identifying antigen was dissolved in, and mixed with, it (in the case of B, fipronil was contained). Immediately, the antibody stick was fit to the reaction container and the antigen-antibody reaction was carried out at 25° C. for 10 minutes.

(3) Detection of Change in Coloration

The reaction container and the antibody stick were washed with tap water to remove the identifying antigen not bound to the immobilized antibody. After the residual wash was sufficiently removed, the coloration reagent was added to the reaction container, and the antibody stick was fit thereto, followed by coloration reaction for 10 minutes and subsequent visual judgment. From data (not shown) thus obtained, it was revealed that the sample soil exhibits the same degree of coloration as in the positive control (containing 0.020 ppm fipronil, corresponding to a concentration of 1.0 ppm fipronil in soil), and with the concentration of 1 ppm fipronil as standard, the concentration of fipronil in soil can be qualitatively judged.

EXAMPLE 6

Then, a specific example of the measurement kit and measurement method for measuring fipronil in soil is specifically described. A fipronil measurement kit comprising a combination of measurement means consisting of the respective units comprises a reagent constitution as shown in Table 4. The procedure of visually judging the concentration of fipronil in soil by using this measurement kit is described. The fipronil used herein was formed into a microcapsule preparation.

TABLE 4

| Unit and reagent constitution | Volume | Number |
|---|---|---|
| Extraction bottle (containing 3 mL of dehydrated ethanol) | 50 mL | 1 bottle |
| Dissolving reagent (containing 6% ethanol) | 3 mL | 1 bottle |
| Reaction container (containing lyophilized fipronil derivative conjugated with horseradish peroxidase) A: for negative control (0 ppm fipronil) B: for positive control (containing 0.020 ppm fipronil) C: for sample measurement | 1 mL for each | 1 container for each |
| Antibody stick (anti-fipronil antibody is immobilized, blocked and then air-dried) | — | 3 sticks |
| Coloration reagent (containing 3,3',5,5'-tetramethylbenzidine solution) | 4 mL | 1 bottle |

(1) Preparation of Sample Solutions 1 g of sample soil (microcapsulated fipronil (corresponding to 1 ppm fipronil) and 10% organic matter) was weighed out and transferred to the extraction container, and stirred for 1 minute in 3 mL of 100% ethanol to extract fipronil contained therein. Tap water was added to the extraction container to give 50 mL of mixture, and its supernatant was used as a sample solution.

(2) Antigen-Antibody Reaction 1 mL dissolving reagent was added to the reaction containers A and B, and 1 mL of sample solution was added to the reaction container C, and the previously encapsulated identifying antigen was dissolved in, and mixed with, it (in the case of B, fipronil was contained). Immediately, the antibody stick was fit to the reaction container and the antigen-antibody reaction was carried out at 25° C. for 10 minutes.

(3) Detection of Change in Coloration

The reaction container and the antibody stick were washed with tap water to remove the identifying antigen not bound to the immobilized antibody. After the residual wash was sufficiently removed, the coloration reagent was added to the reaction container, and the antibody stick was fit thereto, followed by coloration reaction for 10 minutes and subsequent visual judgment. From data (not shown) thus obtained, it was revealed that the sample soil exhibits the same degree of coloration as in the positive control (containing 0.020 ppm fipronil, corresponding to a concentration of 1.0 ppm fipronil in soil), and with the concentration of 1 ppm fipronil as standard, the concentration of fipronil in soil can be qualitatively judged.

In Example 4, the detection of a change in coloration is carried out by visual judgment, but may be carried out in the same manner as in Example 1 by determining the absorbance at 650 nm after the coloration reaction.

The anti-fipronil antibody used in Examples 3 to 6 was the antibody obtained in Example 1.

EXAMPLE 7

A imidacloprid measurement kit comprising a combination of measurement means consisting of the respective units, to which ELISA was applied, specifically comprises a reagent constitution as shown in Table 5. This measurement kit was used to verify the measurement range of imidacloprid.

TABLE 5

| Unit | Reagent constitution |
| --- | --- |
| Reaction unit (reaction container) | Lyophilized imidacloprid derivative conjugated with horseradish peroxidase is contained. |
| Fixing member (antibody stick) | Anti-imidacloprid antibody is immobilized, blocked and then air-dried. |
| Detection unit (coloration reagent) | 3,3',5,5'-Tetramethylbenzidine solution is contained as coloration reagent. |

(1) Preparation of Standard Solutions

A imidacloprid standard reagent (manufactured by Wako Pure Chemical Industries, Ltd.) was dissolved in methanol and diluted with purified water to give 5% methanol solution from which standard dilution series of 0.0002, 0.0004, 0.0008, 0.0016, 0.0031, 0.0063, 0.0125, 0.025, 0.05, and 0.1 ppm were prepared.

(2) Antigen-Antibody Reaction 1 mL of each standard solution was added to the reaction container, and the previously encapsulated identifying antigen was dissolved in, and mixed with, the standard solution. Immediately, the antibody stick was fit to the reaction container and the antigen-antibody reaction was carried out at 25° C. for 10 minutes.

(3) Detection of Change in Coloration

Figure 3:
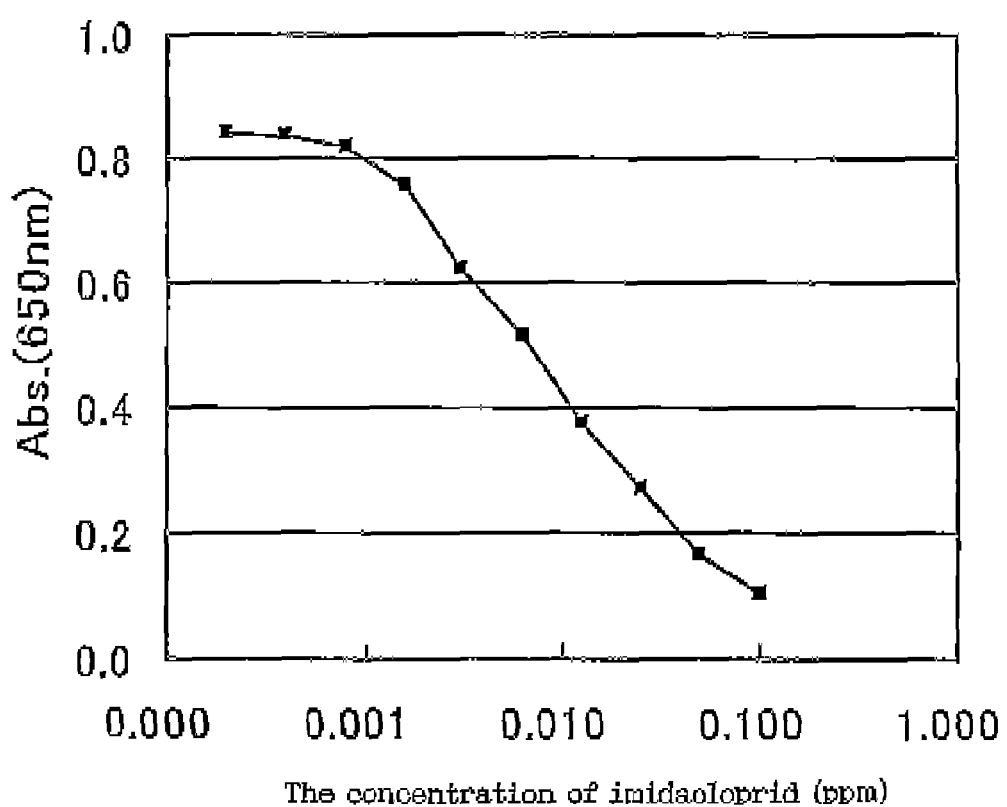
FIG. 3 is a standard curb resulting from a measurement of imidacloprid with the use of measurement kit of the present invention.

The reaction container and the antibody stick were washed with tap water to remove the identifying antigen not bound to the immobilized antibody. After the residual wash was sufficiently removed, the coloration reagent was added to the reaction container, and the antibody stick was fit thereto, followed by coloration reaction for 10 minutes to determine the absorbance at 650 nm. The result revealed that as shown in FIG. 3, imidacloprid can be measured at 0.002 to 0.05 ppm in an almost linear standard curve. Accordingly, visual judgment is feasible in this measurement range.

EXAMPLE 8

Then, a specific example of the measurement kit and measurement method for measuring imidacloprid in soil is specifically described. A imidacloprid measurement kit comprising a combination of measurement means consisting of the respective units comprises a reagent constitution as shown in Table 6. Using this measurement kit, imidacloprid in soil was actually measured.

TABLE 6

| Unit | Reagent constitution |
| --- | --- |
| Extraction unit (extraction bottle) | 5 mL of 50% methanol is contained |
| Dissolving reagent | 5% methanol is contained |
| Reaction unit (reaction container) | Lyophilized imidacloprid derivative conjugated with horseradish peroxidase is contained |
| Fixing member (antibody stick) | Anti-imidacloprid antibody is immobilized, blocked and then air-dried. |

TABLE 6-continued

| Unit | Reagent constitution |
| --- | --- |
| Detection unit (coloration reagent) | 3,3',5,5'-Tetramethylbenzidine solution is contained as coloration reagent. |

(1) Preparation of Sample Solutions 1 g of sample soil (containing 1 ppm imidacloprid and 10% organic matter) was weighed out and transferred to the extraction container, and stirred for 1 minute in 5 mL of 50% methanol to extract imidacloprid contained therein. Tap water was added to the extraction container to give 50 mL of mixture, and its supernatant was used as a sample solution.

(2) Antigen-Antibody Reaction 1 mL of the sample solution or standard solution was added to the reaction container, and the previously encapsulated identifying antigen was dissolved in, and mixed with, the sample solution or standard solution. Immediately, the antibody stick was fit to the reaction container and the antigen-antibody reaction was carried out at 25° C. for 10 minutes.

(3) Detection of Change in Coloration

The reaction container and the antibody stick were washed with tap water to remove the identifying antigen not bound to the immobilized antibody. After the residual wash was sufficiently removed, the coloration reagent was added to the reaction container, and the antibody stick was fit thereto, followed by coloration reaction for 10 minutes to determine the absorbance at 650 nm.

The standard solution was used to prepare a calibration curve, and the concentration of imidacloprid recovered from the sample soil was determined. As a result, the concentration of imidacloprid in soil was accurately determined to be 1 ppm.

EXAMPLE 9

Then, a specific example of the measurement kit and measurement method for visually judging imidacloprid in soil is specifically described. A imidacloprid measurement kit comprising a combination of measurement means consisting of the respective units comprises a reagent constitution as shown in Table 7. The procedure of visually judging the concentration of imidacloprid in soil by using this measurement kit is described.

TABLE 7

| Unit and reagent constitution | Volume | Number |
| --- | --- | --- |
| Extraction bottle (containing 5 mL of 50% methanol) | 50 mL | 1 bottle |
| Dissolving reagent (containing 5% methanol) | 3 mL | 1 bottle |
| Reaction container (containing lyophilized imidacloprid derivative conjugated with horseradish peroxidase) A: for negative control (0 ppm imidacloprid) B: for positive control (containing 0.020 ppm imidacloprid) C: for sample measurement | 1 mL for each | 1 container for each |
| Antibody stick (anti-imidacloprid antibody is immobilized, blocked and then air-dried) | — | 3 sticks |
| Coloration reagent (containing 3,3',5,5'-tetramethylbenzidine solution) | 4 mL | 1 bottle |

(1) Preparation of Standard Solutions 1 g of sample soil (containing 1 ppm imidacloprid and 10% organic matter) was weighed out and transferred to the extraction container, and stirred for 1 minute in 5 mL of 50% methanol to extract imidacloprid contained therein. Tap water was added to the extraction container to give 50 mL of mixture, and its supernatant was used as a sample solution.

(2) Antigen-Antibody Reaction 1 mL of dissolving reagent was added to the reaction containers A and B, and 1 mL of sample solution was added to the reaction container C, and the previously encapsulated identifying antigen was dissolved in, and mixed with, it (in the case of B, imidacloprid was contained). Immediately, the antibody stick was fit to the reaction container and the antigen-antibody reaction was carried out at 25° C. for 10 minutes.

(3) Detection of Change in Coloration

The reaction container and the antibody stick were washed with tap water to remove the identifying antigen not bound to the immobilized antibody. After the residual wash was sufficiently removed, the coloration reagent was added to the reaction container, and the antibody stick was fit thereto, followed by coloration reaction for 10 minutes and subsequent visual judgment. From data (not shown) thus obtained, it was revealed that the sample soil exhibits the same degree of coloration as in the positive control (containing 0.020 ppm imidacloprid, corresponding to a concentration of 1.0 ppm imidacloprid in soil), and with the concentration of 1 ppm imidacloprid as standard, the concentration of imidacloprid in soil can be qualitatively judged.

EXAMPLE 10

Then, a specific example of the measurement kit and measurement method for measuring imidacloprid in soil is specifically described. A imidacloprid measurement kit comprising a combination of measurement means consisting of the respective units comprises a reagent constitution as shown in Table 8. The procedure of visually judging the concentration of imidacloprid in soil by using this measurement kit is described. The imidacloprid used herein was formed into a microcapsule preparation.

TABLE 8

| Unit and reagent constitution | Volume | Number |
|---|---|---|
| Extraction bottle (containing 3 mL of dehydrated ethanol) | 50 mL | 1 bottle |
| Dissolving reagent (containing 6% ethanol) | 3 mL | 1 bottle |
| Reaction container (containing lyophilized imidacloprid derivative conjugated with horseradish peroxidase) A: for negative control (0 ppm imidacloprid) B: for positive control (containing 0.020 ppm imidacloprid) C: for sample measurement | 1 mL for each | 1 container for each |
| Antibody stick (anti-imidacloprid antibody is immobilized, blocked and then air-dried) | — | 3 sticks |
| Coloration reagent (containing 3,3',5,5'-tetramethylbenzidine solution) | 4 mL | 1 bottle |

(1) Preparation of Sample Solutions 1 g of sample soil (microcapsulated imidacloprid (corresponding to 1 ppm imidacloprid) and 10% organic matter) was weighed out and transferred to the extraction container, and stirred for 1 minute in 3 mL of 100% ethanol to extract imidacloprid contained therein. Tap water was added to the extraction container to give 50 mL mixture, and its supernatant was used as a sample solution.

(2) Antigen-Antibody Reaction 1 mL of dissolving reagent was added to the reaction containers A and B, and 1 mL of sample solution was added to the reaction container C, and the previously encapsulated identifying antigen was dissolved in, and mixed with, it (in the case of B, imidacloprid was contained). Immediately, the antibody stick was fit to the reaction container and the antigen-antibody reaction was carried out at 25° C. for 10 minutes.

(3) Detection of Change in Coloration

The reaction container and the antibody stick were washed with tap water to remove the identifying antigen not bound to the immobilized antibody. After the residual wash was sufficiently removed, the coloration reagent was added to the reaction container, and the antibody stick was fit thereto, followed by coloration reaction for 10 minutes and subsequent visual judgment. From data (not shown) thus obtained, it was revealed that the sample soil exhibits the same degree of coloration as in the positive control (containing 0.020 ppm imidacloprid, corresponding to a concentration of 1.0 ppm imidacloprid in soil), and with the concentration of 1 ppm imidacloprid as standard, the concentration of imidacloprid in soil can be qualitatively judged.

In Example 8, the detection of a change in coloration is carried out by visual judgment, but may be carried out in the same manner as in Example 5 by determining the absorbance at 650 nm after the coloration reaction.

The anti-imidacloprid antibody used in Examples 7 to 10 was the antibody obtained in Example 2.

What is claimed is:

1. A kit for measurement of an active ingredient of a termite insecticide by an immunoassay method, comprising:
   1) an extraction unit for extracting, with a solvent, a termite insecticide active ingredient from an object of measurement and
   2) a reaction unit including
      i) a reaction container for encapsulating an identifying antigen, which is a conjugate consisting of a hapten of the termite insecticide active ingredient and a substance having an identifying function,
      ii) a fixing member for immobilizing an antibody that is specific for an active ingredient, and
      iii) a sealing member capable of fitting to the reaction container.

2. The kit for measurement of an active ingredient of a termite insecticide by the immunoassay method of claim 1, wherein said antibody is a monoclonal antibody or a fragment thereof.

3. The kit for measurement of an active ingredient of a termite insecticide by the immunoassay method of claim 1, wherein said reaction unit includes
   a combination of
      a) at least one first reaction container in which the identifying antigen is encapsulated, and
      b) at least one second reaction container in which a mixture of the identifying antigen and a known amount of the termite insecticide active ingredient are encapsulated;
   ii) a fixing member for immobilizing an antibody that is specific for the active ingredient; and
   iii) sealing members capable of fitting to the first and second reaction containers.

4. The kit for measurement of an active ingredient of a termite insecticide by the immunoassay method according to claim 3, wherein the identifying antigen and a mixture of the identifying antigen and a termite insecticide active ingredient of known amount are previously encapsulated in a dried state in the first and second reaction containers and such that in the first reaction container in which only the identifying antigen is encapsulated, the identifying antigen can be dissolved by a sample solution, and in the second reaction container in which the mixture is encapsulated, the mixture can be dissolved by a dissolving liquid.

5. The kit for measuring an active ingredient of a termite insecticide by using the immunoassay method according to claim 1, wherein said reaction unit also has a detection function for visually or optically detecting a change depending on the concentration of a termite insecticide active ingredient in a sample.

6. The kit for measuring an active ingredient of a termite insecticide by using the immunoassay method according to claim 1, wherein said kit further includes a detection unit for visually or optically detecting a change depending on the concentration of a termite insecticide active ingredient in a sample.

7. The kit for measuring an active ingredient of a termite insecticide by using the immunoassay method according to claim 1, wherein said kit further includes a dilution unit for diluting a sample solution extracted in the extraction unit to a predetermined ratio.

8. The kit for measurement of an active ingredient of a termite insecticide by using the immunoassay method according to claim 1, wherein said extraction unit includes a solvent for extracting the active ingredient from the subject of measurement.

9. The kit for measurement of an active ingredient of a termite insecticide by using the immunoassay method of claim 8, wherein said solvent is one selected from the group consisting of ethanol, methanol and dimethyl sulfoxide, or a mixture of two or more thereof.

10. The kit for measurement of an active ingredient of a termite insecticide by using the immunoassay method according to claim 1, wherein said object of measurement is a material contained in a capsule preparation.

11. The kit for measurement of an active ingredient of a termite insecticide by using the immunoassay method of claim 10, wherein said capsule preparation is in the form of a microcapsule.

12. The kit for measurement of an active ingredient of a termite insecticide by using the immunoassay method according to claim 1, wherein said termite insecticide active ingredient is fipronil or imidacloprid.

* * * * *